US00PP25023P3

(12) United States Plant Patent
Layt

(10) Patent No.: US PP25,023 P3
(45) Date of Patent: Nov. 4, 2014

(54) ***CALLISTEMON VIMINALIS* PLANT NAMED 'CC19'**

(50) Latin Name: *Callistemon viminalis*
Varietal Denomination: CC19

(71) Applicant: Todd Layt, Richmond (AU)

(72) Inventor: Todd Layt, Richmond (AU)

( * ) Notice: Subject to any disclaimer, the term of this patent is extended or adjusted under 35 U.S.C. 154(b) by 133 days.

(21) Appl. No.: 13/694,559

(22) Filed: Dec. 12, 2012

(65) Prior Publication Data

US 2014/0165243 P1 Jun. 12, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt

(57) ABSTRACT

'CC19' is a distinctive variety of *Callistemon viminalis* which is characterized by the combination of a short height, finer textured foliage, auburn color of immature foliage and stability and uniformity of traits through successive cycles of asexual propagation.

3 Drawing Sheets

Latin name of the genus and species: The Latin name of the genus and species of the novel variety disclosed herein is *Callistemon viminalis*.

Variety denomination: The inventive variety of *Callistemon viminalis* disclosed herein has been given the variety denomination 'CC19'.

BACKGROUND OF THE INVENTION

The present invention relates to a new and distinct perennial variety of *Callistemon viminalis*, which has been given the variety denomination of 'CC19'. Its market class is that of an ornamental shrub. 'CC19' is intended for use in landscaping as a hedge shrub.

Parentage: The *Callistemon viminalis* variety 'CC19' was the result of open pollination of *Callistemon viminalis* 'Captain Cook' (unpatented) and was discovered at a commercial breeding facility in Clarendon, New South Wales, Australia. In 2006 seed was collected from *Callistemon viminalis* 'Captain Cook' plants and many seedlings were grown. From these seedlings, eight plants were selected for further testing. In 2009 a final selection took place and one plant was then selected as the final candidate due to the combination of a short height, fine textured foliage, and auburn color of immature foliage. The plant was given the name 'CC19'.

Asexual Reproduction: 'CC19' was grown to a mature age and was found to grow uniform and 4 successive cycles of vegetative asexual propagation at a commercial breeding facility in Clarendon, New South Wales, Australia have proven to be true to type.

SUMMARY OF THE INVENTION

'CC19' is a distinctive variety of *Callistemon viminalis* which is characterized by the combination of a short height, fine textured foliage, and auburn color of immature foliage.

BRIEF DESCRIPTION OF THE FIGURES

FIG. 1 shows two 'CC19' plants, at far left and center, in the ground and unpruned, at approximately 3 years old with

*Callistemon viminalis* 'Little John', on the far right, shown for comparison. Note that 'CC19' has auburn immature foliage and bright green mature foliage compared to the greyed green foliage of 'Little John'. It is also apparent that the foliage of 'CC19' has a much finer texture when compared with that of 'Little John'

Figure 1:
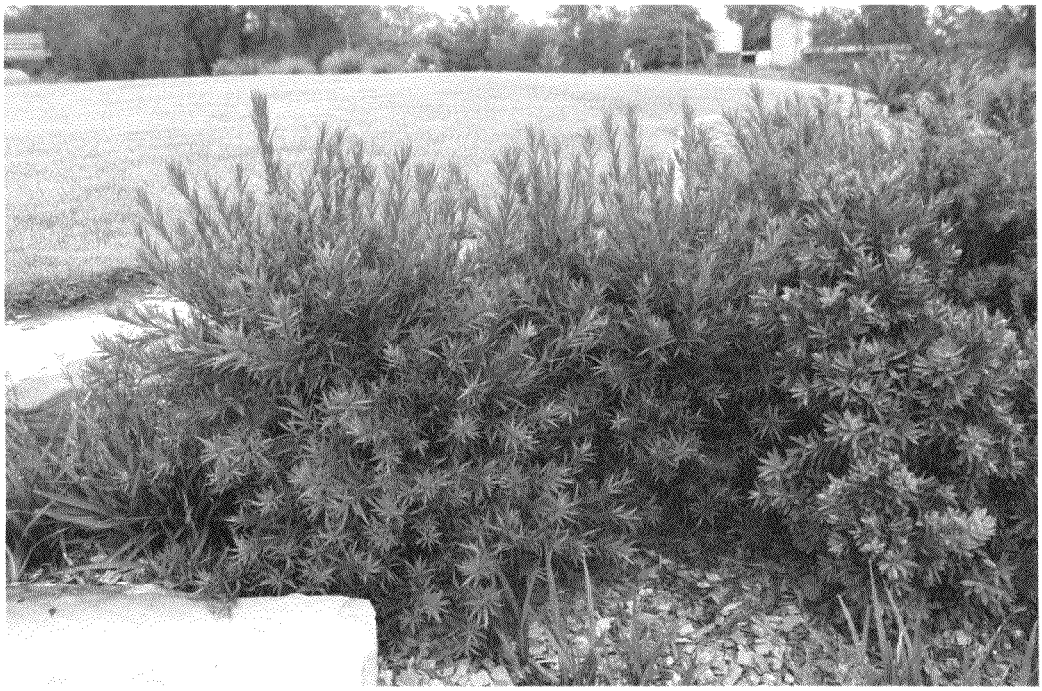
Figure 2:
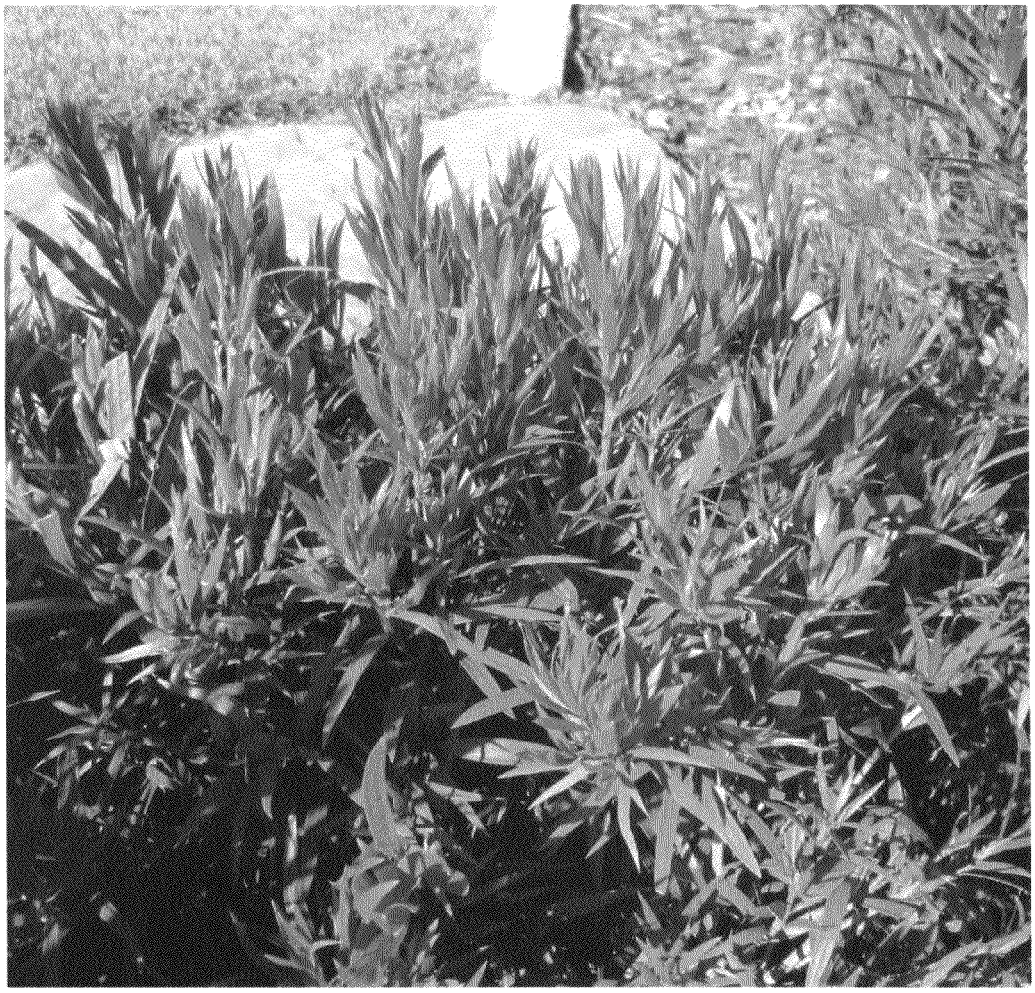

FIG. 2 shows the auburn colored new growth of 'CC19'

Figure 3:
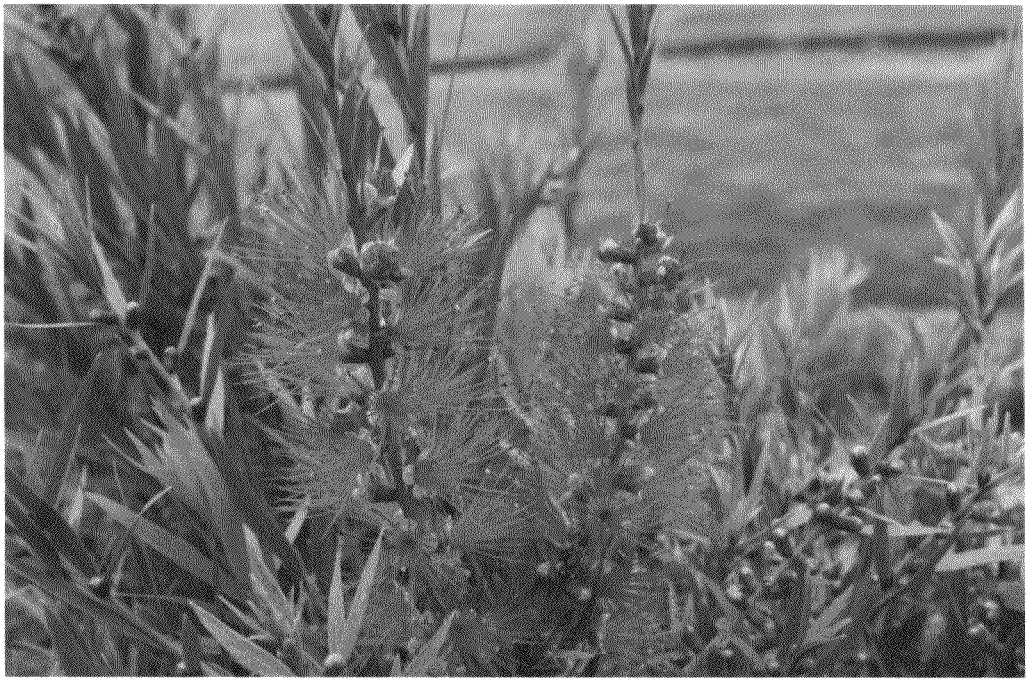

FIG. 3 shows a typical inflorescence spike of 'CC19'

BOTANICAL DESCRIPTION OF THE PLANT

The following is a detailed botanical description of a new and distinct variety of *Callistemon viminalis* known as 'CC19' based upon observations of 24-month old plants grown from rooted cuttings into 200 mm nursery pots in full sun in open beds in Clarendon, New South Wales, Australia during spring 2009-summer 2010. Unless indicated otherwise, the descriptions disclosed herein are based upon observations made from mature 'CC19' plants grown in full sun from rooted cuttings filled with soilless potting media, maintained with granular slow release fertilizer, and regularly watered with overhead irrigation. No pest and disease measures were taken. Observation data was recorded in summer of 2010.

Those skilled in the art will appreciate that certain characteristics will vary with older or, conversely, with younger plants. 'CC19' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2001 edition.

A botanical description of 'CC19' and comparisons with other varieties of *Callistemon viminalis* are provided below.

Technical Description of the Variety.

Plant description:

*Plant habit*.—Shrub; erect to semi erect, rounded and dense.

*Height*.—Approximately 100 to 150 cm.

*Width*.—Approximately 100 to 150 cm.

*Bloom period*.—Spring.

*Hardiness*.—USDA Zone 8 to 11.

*Environmental tolerances*.—Similar to the parent plants; tolerates light shade, a wide range of soil conditions and drought tolerant once established.

*Pest and disease susceptibility or resistance*.—In common with the species, none of note.

*Propagation*.—Propagation is accomplished using softwood cuttings. Roots well without rooting compound or hormone.

*Time to develop roots*.—2 to 4 weeks.

*Crop time*.—Approximately 12 months are needed to produce a 14-centimeter container with plant in flower, starting from a rooted cutting.

Stem:

*Branching and habit*.—Strong branching habit; branch angles acute, branch attitude is erect to semi erect

*Stem strength*.—Woody and strong.

*Shape*.—Cylindrical.

*Stem color*.—Immature stem is closest to greyed orange RHS 168D. Mature basal stem color is closest to grey brown RHS 199D.

*Stem dimensions*.—Basal stems reach approximately 27 to 32 cm in so length before branching; diameter is approximately 7 mm near the base.

*Stem surface*.—Corky, smooth. Immature stems are lightly pubescent while mature stems are glabrous.

*Internode length*.—Ranges from 10 to 15 mm.

Foliage:

*Type*.—Evergreen.

*Shape*.—Lanceolate.

*Division*.—Simple.

*Apex*.—Acute.

*Base*.—Cunneate.

*Venation*.—Pinnate.

*Vein color* (*adaxial surfaces*).—147A.

*Vein color* (*abaxial surfaces*).—137A.

*Margins*.—Mature margin is entire; immature margin is ciliate.

*Arrangement*.—Alternate.

*Attachment*.—Sessile.

*Texture*.—Leathery.

*Surfaces* (*adaxial surface*).—Juvenile: lightly pubescent; mature: glabrous.

*Surfaces* (*abaxial surface*).—Juvenile: lightly pubescent; mature: glabrous.

*Mature leaf dimensions*.—Average length 59.2 mm, average width 6.6 mm.

*Leaf color* (*adaxial surface*).—Juvenile: varies from greyed orange 167B to greyed orange 174A; mature: 137A.

*Leaf color* (*abaxial surface*).—Juvenile: varies from greyed orange 167B to greyed orange 174A; mature: a slightly darker hue of 137A in comparison with the adaxial surface.

*Petiole*.—None.

*Stipules*.—None.

Inflorescence:

*Inflorescence*.—Indeterminate, leafy spikes ranging in length from 8 to 12 cm and an approximate width of 6 cm, comprised of many small, sessile florets with exserted stamens.

*Flowers*.—Sessile. Sepals are immeasurably minute. Inconspicuous corolla comprised of five unfused petals; diameter across corolla is 9 to 11 mm (average of 10 mm). Color of the corolla approximates to yellow-green (RHS 154C or 154D). Non fragrant. Flowers of *Callistemon* are distinguished by their brightly colored, exserted stamen which give the spike a bottlebrush appearance.

*Bud*.—Many tightly grouped oblong or ovoid axillary buds measuring approximately 7 mm long and 3 mm wide prior to bud swell. Color approximates to 146B prior to bud swell.

Reproductive organs:

*Stamens*.—Many; greater than 50.

*Stamen color*.—47B.

*Stamen dimensions*.—18 to 21 mm in length (average length is 18.4 mm) and very thin.

*Attachment*.—Each stamen joins floral tube independently: Free.

*Anther dimensions*.—Minute.

*Anther color*.—Yellow.

*Pollen*.—Present.

*Pistil*.—One.

*Pistil dimensions*.—About 20 mm in length and very thin.

*Pistil color*.—47B.

*Ovary position*.—Half-Inferior.

Fruit and seed production: Dehescent flowers reveal round, slightly oblong seed capsules grouped tightly along the stem. Sessile. Dimensions are 3 to 5 mm in diameter and 4 to 5 mm in length. Color at maturity approximates to brown 200A. Seeds are many and minute with a color close to greyed orange 166B.

Comparisons with Other *Callistemon*

'CC19' is characterized by the combination of a short height, fine textured foliage, red color of immature foliage when compared to that of parent *Callistemon viminalis* 'Captain Cook' which has a medium plant height and green new foliage. There are three commercially available cultivars, known to the breeder, that have a similar habit and size as 'CC19': *Callistemon viminalis* 'Matthew Flinders' (U.S. Plant Pat. No. 17,314) and *Callistemon viminalis* 'Little Silver' (unpatented) and *Callistemon viminalis* 'Little Caroline' (unpatented).

When compared with 'Captain Cook', 'CC19' has a plant height of approximately 1 to 1.5 m whereas 'Captain Cook' is approximately 2 m high. The foliage dimensions of 'Captain Cook' are similar to that of 'CC19' as is the mature foliage color however the immature foliage of 'CC19' is greyed orange 167B to greyed orange 174A in color whereas the immature foliage color of 'Captain Cook' is yellow green 144B.

The cultivars 'Matthew Flinders', 'Little Caroline' and 'Little Silver' all have a height and habit similar to that of 'CC19' and the mature foliage color of each cultivar is a similar hue of green with only negligible differences between them. However, the unique greyed orange color of the immature foliage of 'CC19' is the primary distinguishing characteristic. The immature foliage of 'CC19' has a color palette that ranges from greyed orange 167B to greyed orange 174A whereas the immature foliage color of each of the three cultivars listed above are all a very similar shade of yellow green that approximates to RHS 144B.

'CC19' also has notably finer foliage texture. Using the foliage length-to-width ratio as a metric, 'CC19' has the finest foliage of all three comparators. 'CC19' has a foliage length-to-width ratio of 8.97 (with an average length of 59.2 mm and average width of 6.6 mm) whereas the calculated ratio for cultivars 'Matthew Flinders', 'Little Caroline' and 'Little Silver', respectively, are 5.33 (average length of 32.0 mm and width of 6.0 mm), 5.37 (average length of 45.4 mm and width of 8.4 mm), and 6.12 (average length of 52.2 mm and width of 8.2 mm).

That which is claimed is:

1. A new and distinct variety of *Callistemon viminalis* plant named 'CC19', substantially as described and illustrated herein.

* * * * *